United States Patent [19]

Durden, Jr.

[11] 4,071,627
[45] Jan. 31, 1978

[54] 2-OXIMINO-TETRAHYDRO-1,4-THIAZIN-5-ONE COMPOUNDS AND PESTICIDAL CARBAMATE DERIVATIVES

[75] Inventor: John Apling Durden, Jr., South Charleston, W. Va.

[73] Assignee: Union Carbide Corporation, New York, N.Y.

[21] Appl. No.: 727,634

[22] Filed: Sept. 29, 1976

[51] Int. Cl.$^2$ .................... C07D 279/12; A01N 9/12
[52] U.S. Cl. ...................................... 424/246; 544/58
[58] Field of Search .................... 260/243 R; 424/246

[56] References Cited

U.S. PATENT DOCUMENTS

| | | | |
|---|---|---|---|
| 3,790,566 | 2/1974 | Bellina | 260/243 |
| 4,003,895 | 1/1977 | Durden | 260/243 |
| 4,003,897 | 1/1977 | Durden | 260/243 |

*Primary Examiner*—John M. Ford
*Attorney, Agent, or Firm*—Richard C. Stewart

[57] ABSTRACT

2-Oximino-tetrahydro-1,4-thiazin-5-one compounds are useful as intermediates in the preparation of 2-carbamoyloximino-tetrahydro-1,4-thiazin-5-one carbamate compounds that exhibit outstanding pesticidal activity.

46 Claims, No Drawings

2-OXIMINO-TETRAHYDRO-1,4-THIAZIN-5-ONE COMPOUNDS AND PESTICIDAL CARBAMATE DERIVATIVES

This invention relates to 2-oximino-tetrahydro-1,4-thiazin-5-one oxime and 2-carbamoyloximino-tetrahydro-1,4-thiazin-5-one carbamate compounds and to their preparation. This invention is also directed to insecticidal and miticidal compositions comprising an acceptable carrier and an insecticidally and miticidally effective amount of a carbamate compound of this invention as well as to a method of controlling insects and mites by subjecting them to an insecticidally or miticidally effective amount of a carbamate compound of this invention.

More particularly, this invention relates to compounds of the formula:

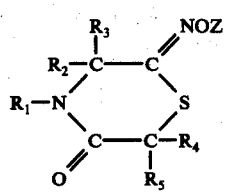

wherein:

$R_1$, $R_2$, $R_3$, $R_4$ and $R_5$ are individually hydrogen or alkali;
wherein

Z is hydrogen or
$R_6$ and $R_7$ are individually hydrogen, alkenyl, alkynyl, phenylalkyl or either substituted or unsubstituted alkyl or phenyl wherein the permissible substituents are one or more fluoro, chloro, bromo, nitro, cyano, alkyl, alkoxy, alkylthio, alkylsulfinyl, alkylsulfonyl, carbamoyl, alkylcarbamoyl or dialkylcarbamoyl substituents; or when $R_6$ is other than hydrogen $R_7$ may also be alkanoyl, trihalomethanesulfenyl, dialkylaminosulfenyl, morpholinosulfenyl, pyrrolidylsulfenyl, piperidylsulfenyl, or either substituted or unsubstituted phenylsulfenyl wherein the permissible substituents are one or more fluoro, chloro, bromo, nitro, cyano, alkoxy, alkyl, dialkylamino, trihalomethyl, alkylthio, alkylsulfinyl or alkylsulfonyl substituents in any combination.

In general, $R_1$, $R_2$, $R_3$, $R_4$ and $R_5$ substituents individually may not include more than eight aliphatic carbons and $R_6$ and $R_7$ individually may not include more than eighteen carbons. Preferred either because of their higher level of pesticidal activity or because of their usefulness as intermediates in the preparation of carbamate compounds that exhibit outstanding pesticidal activity are the compounds of this invention in which:

$R_1$, $R_2$, $R_3$, $R_4$ and $R_5$ are individually hydrogen, methyl or ethyl;
Z is hydrogen or

wherein:

$R_6$ is alkyl having from 1 to 4 carbons.
$R_7$ is hydrogen, alkyl, trihalomethanesulfenyl, dialkylaminosulfenyl, morpholinosulfenyl, pyrrolidylsulfenyl, piperidylsulfenyl or either substituted or unsubstituted phenylsulfenyl wherein the permissible substituents are one or more chloro, bromo, fluoro, nitro, cyano, alkoxy, alkyl, alkylthio, alkylsulfinyl, alkylsulfonyl substituents in any combination;

The carbamate compounds of this invention are those of the above formula in which Z is

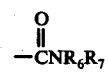

and $R_1$, $R_2$, $R_3$, $R_4$, $R_5$, $R_6$ and $R_7$ are as described above. These compounds exhibit outstanding miticidal and insecticidal activity and may be used as miticides and insecticides utilizing those methods known to those skilled in the pesticidal art. They are also relatively non-toxic to plants and mammals when used in amounts sufficient to kill insects and mites.

The oxime compounds of this invention are those of the above formula in which Z is hydrogen and $R_1$, $R_2$, $R_3$, $R_4$ and $R_5$ are as described above. These compounds are useful as intermediates in the preparation of the insecticidally and miticidally active carbamate compounds of this invention. An oxime compound according to this invention can be reacted with an appropriately substituted carbamoyl halide in the presence of a suitable acid acceptor to produce the corresponding carbamate compound. For example, 2-oximino-3,3-dimethyltetrahydro-1,4-thiazin-5-one can be reacted with N-methyl-N-(trichloromethylsulfenyl) carbamoyl fluoride in the presence of triethylamine as an acid acceptor, to produce 2[O-(N-methyl-N-trichloromethanesulfenyl carbamoyl)oximino]-3,3-dimethyltetrahydro-1,4-thiazin-5-one, the corresponding insecticidally and miticidally active carbamate compound. The oxime compounds of this invention can also be reacted with other chemical species containing electron deficient reaction sites, such as isocyanates or phosgene followed by reaction with an appropriately substituted amine, to produce insecticidally and miticidally active carbamate compounds. The above disclosed reactions are described in more detail below.

The compounds of this invention can be prepared in accordance with a variety of methods. Three preferred methods for preparing the oxime compounds of this invention are illustrated by the general reaction schemes set forth below in which $R_1$, $R_2$, $R_3$, $R_4$ and $R_5$ are as described above, M is an alkali metal cation, $R_8$ is alkyl and Y is nitro, methylsulfonyl or any other appropriate leaving group known to those skilled in the art;

METHOD I

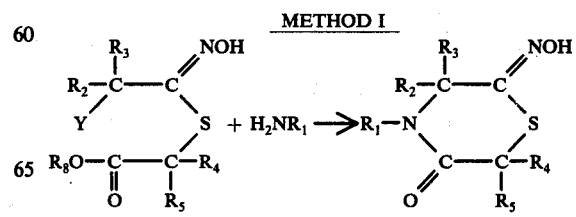

METHOD II

-continued

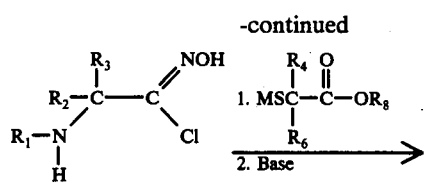

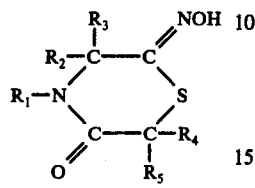

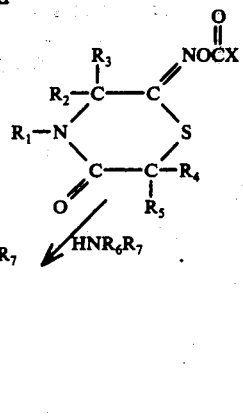

In Method IV, $R_6$ and $R_7$ are individually hydrogen, alkenyl, alkynyl, phenylalkyl or either substituted or unsubstituted phenyl or alkyl.

METHOD III

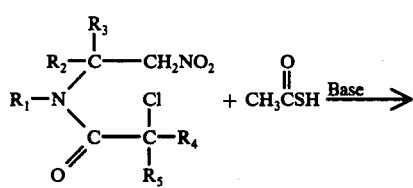

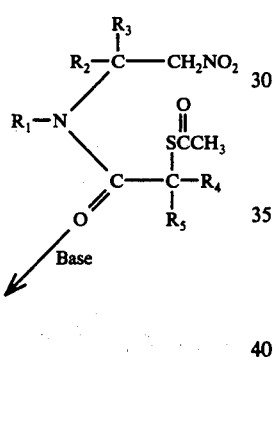

METHOD V

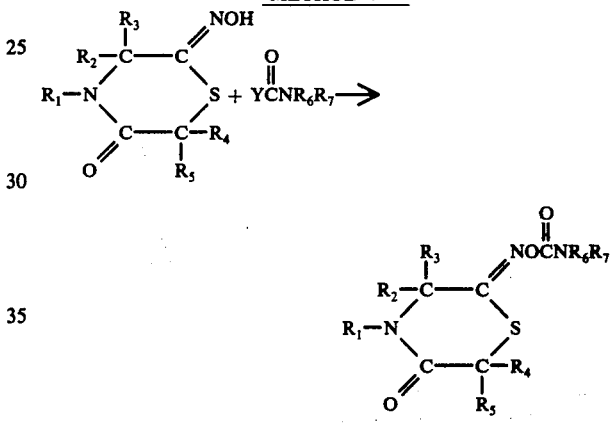

The carbamate compounds of this invention can be prepared according to a variety of methods which utilize the oxime compounds of this invention as precursors. Three preferred methods are illustrated by the reaction schemes set forth below in which $R_1$, $R_2$, $R_3$, $R_4$, $R_5$, $R_6$ and $R_7$ are as described above and X is chlorine or fluorine, except as noted:

METHOD VI

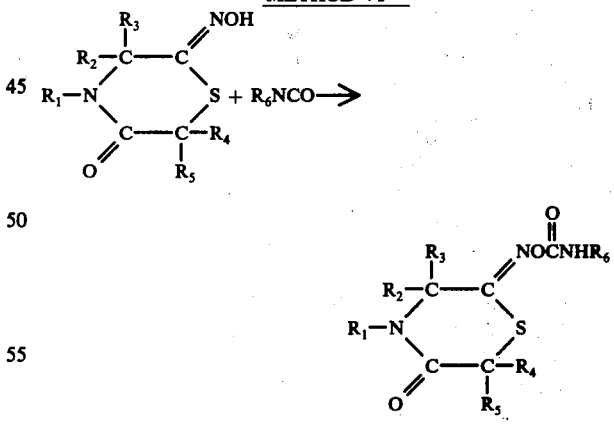

In Method VI, $R_6$ is alkenyl, alkynyl, phenylalkyl or either substituted or unsubstituted alkyl or phenyl.

The reactions illustrated in Methods, I, II, III, IV, V and VI may be conducted under somewhat similar reaction conditions in that:

a. Substantially equimolar amounts of the reactants are usually brought together in an inert solvent. However, although it should be understood that in some cases the reactants themselves may function as the solvent medium. Any inert solvent such as benzene, tolu-

METHOD IV

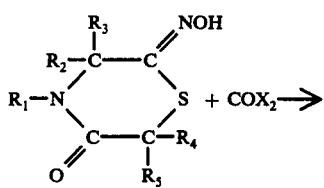

ene, xylene, dioxane, tetrahydrofuran or the like can be used.

b. Reaction temperatures are not critical and can be varied over a wide range depending to a large extent on the reactivity and the stability of the reactants. Preferred reaction temperatures are from about −30° C. to about 100° C.

c. Reaction pressures are not critical. For convenience the reaction is usually conducted at atmospheric or autogeneous pressure.

The reactions of Methods I, II, III, IV, V and VI can be conducted in a homogeneous phase system or a heterogeneous phase system. In the latter case phase transfer agents such as crown ether compounds, quaternary ammonium halide compounds or the like, may be used to facilitate the transfer of the reactants across the phase interface.

The reactions illustrated in Methods IV and V are conducted in the presence of an acid acceptor. The molar ratio of acid acceptor to either reactant is substantially equimolar although a slight excess of acid acceptor may be employed if desired. The acid acceptor employed is a basic material which may be either an organic or an inorganic base. Illustrative of organic bases which are useful as acid acceptors in these reactions are tertiary amines, alkali metal alkoxides or the like. Bases such as potassium hydroxide, sodium hydroxide or the like are illustrative of inorganic bases that can be used as acid acceptors in the conduct of these reactions. Tertiary amines such as trimethylamine, triethylamine, pyridine or 1,4-diazabicyclo[2.2.2]octane and alkali metal hydroxides, such as sodium or potassium hydroxide are preferred acid acceptors in these reactions.

The reaction illustrated in Method VI is preferably conducted in the presence of a quantity of a catalyst sufficient to provide a suitable and reasonable reaction rate. In general, any conventional catalyst of the type commonly employed to promote reactions between isocyanate compounds and compounds that contain an active hydrogen can be used. Illustrative of materials useful as catalyst in the conduct of this reaction are organic bases such as organic amines, alkali metal alkoxides, alkali metal alkylides or the like and inorganic bases such as alkaline earth hydroxides, alkali metal hydroxides and the like. Organic and inorganic acids may also be used as catalyst in this reaction. Preferred catalyst are tertiary amines such as triethylamine, trimethylamine, pyridine or the like.

The reactions illustrated in Methods II and III are conducted in the presence of a base. The molar ratio of base to either reactant is substantially equimolar, although a slight excess of base may be employed if desired. The base employed may be either a strong inorganic base or a strong organic base. Organic bases such as alkali metal alkoxides, alkali metal alkylides or the like and inorganic bases such as alkali metal hydroxides, alkaline earth metal hydroxides or the like are illustrative of bases that can be used in the conduct of these reactions. Preferred bases are potassium and sodium hydroxide.

The carbamate compounds of this invention in which $R_7$ is alkanoyl can be prepared by reacting the corresponding carbamate compound in which $R_7$ is hydrogen with an appropriately substituted alkanoyl halide or an anhydride, or, alternatively by the reaction illustrated in Method V wherein $R_7$ is an alkanoyl function.

The carbamate compounds of this invention wherein $R_6$ and/or $R_7$ include either an alkylsulfinyl or an alkylsulfonyl moiety can be prepared by the oxidation of the corresponding alkylthio moiety with a mild oxidizing agent, as for example peracetic acid, at an appropriate point in the synthetic procedure.

The derivatized compounds utilized as reactants in the reaction illustrated in Method I can be prepared in accordance with a variety of conventional methods. For example, 1-alkoxycarbamoylalkylthio-2-nitroalkylaldoxime and 1-alkoxycarbamoylalkylthio-2-methylsulfonylaldoxime compounds can be prepared by reacting the corresponding alkyl 2-mercaptoalkylate with either an appropriately substituted 2-nitroalkylhydroxamoyl chloride or 2-methylsulfonyl hydroxamoyl chloride in the presence of a base such as sodium hydroxide. 2-Nitroalkylhydroxamoyl and 2-methylsulfonylhydroxamoyl chloride compounds, in turn, can be prepared by reacting either the 2-nitroaldoxime or 2-methylsulfonylaldoxime with chlorine in hydrochloric acid solvent.

2-Aminoalkylhydroxamoyl chloride compounds utilized as reactants in the reaction of Method II can be prepared by sequentially treating the corresponding 2-aminoaldoxime with hydrochloric acid and chlorine gas.

The N-nitroalkyl amide compounds utilized as reactants in the reaction illustrated in Method III can be prepared by reacting the corresponding 1-nitro-2-acyloxyalkane with an appropriately substituted amine to form either the corresponding 1-nitro-2-aminoalkane or 1-nitro-2-alkylaminoalkane, either of which in turn can be reacted with an appropriately substituted γ-chloroalkanoylchloride to form the desired product. These procedures are described in more detail in R. L. Heath and J. D. Rose, J. Chem. Soc., 1486 (1947, C. H. Grob and K. Camenisch, Helv. Chem. Acta. 36, 44 (1953), C. A. Grob and K. Camenisch, Helv. Chem. Acta. 38, 1694 (1955) and references cited therein.

2-Oximino-tetrahydro-1,4-thiazin-5-one compounds utilized as reactants in the reactions illustrated in Methods IV, V and VI can be prepared as described hereinabove. Isocyanate, carbonyl chloride, carbonyl fluoride and amine compounds employed as reactants in these reactions are well known compounds that can be either obtained from commercial sources or prepared in accordance with methods well known to those skilled in the synthetic art.

Carbamoyl halide compounds utilized as reactants in the reaction illustrated in Method V can be prepared in accordance with a variety of conventional methods. The choice of method is influenced to a large extent by $R_7$ substituent patterns. One preferred method of preparing carbamoyl fluoride reactants in which $R_7$ is a substituted sulfenyl substituent is by reacting hydrogen fluoride with an appropriately substituted isocyanate to form the mono-substituted carbamoyl fluoride which is then reacted with an appropriately substituted sulfenyl chloride in the presence of an acid acceptor to form the corresponding N-sulfenylated carbamoyl fluoride. For example, hydrogen fluoride can be reacted with methyl isocyanate dissolved in toluene to produce N-methylcarbamoyl fluoride which, in turn, can be reacted with *phenylsulfenyl chloride*, in the presence of essentially an equivalent amount of triethylamine, to produce N-methyl-N-(phenylsulfenyl) carbamoyl fluoride. This procedure is described in more detail in U.S. Pat. No. 3,639,471. The remaining carbamoyl halide reactants in which $R_6$ and/or $R_7$ are bonded to nitrogen through a carbon nitrogen bond can be prepared by reacting an appropriately substituted amine with a carbonyl halide such as phosgene in the presence of an acid acceptor as for example triethylamine.

The following specific examples are presented to more particularly illustrate this invention.

EXAMPLE I

Preparation of 1-(Ethoxycarbonylmethylthio)-2-nitro-2-methylpropionaldoxime

A mixture of 24 g. of ethyl 2-mercaptoacetate, 20 g. of potassium bicarbonate, 75 g of water and 75 ml of ethanol was charged into a flask and stirred. To the mixture was added 33 g of 2-nitro-2-methylpropionhydroxamoyl chloride dissolved in 75 ml of chloroform over a 15 minute period with stirring and cooling to maintain the temperature at 25° C. during the addition. The reaction mixture was stirred over night at 25° C. The ethanol and chloroform was stripped from the reaction mixture and the residue extracted with ethyl ether. The ethyl ether layer was washed with water and dried over $MgSO_3$. After drying the ethyl ether was stripped from the product under reduced pressure to yield 38 g of 1-(ethoxycarbonylmethylthio)-2-nitro-2-methylpropionaldoxime. The NMR and IR spectra agreed with the proposed structure.

EXAMPLE II

Preparation of 2-Oximino-3,3-dimethyltetrahydro-1,4-thiazin-5-one

A mixture of 12 g. of 1-ethoxycarbonylmethylthio-2-nitro-2-methylpropionaldoxime and 150 ml of ammonium hydroxide was charged into a pyrex pressure bottle and stirred at room temperature for three days. The excess ammonia and water was stripped from the reaction mixture under reduced pressure. The solid crystalline residue was washed with a small amount of cold water and dried. The residue was then recrystallized from acetonitrile to yield 4 g of 2-Oximino-3,3-dimethyltetrahydro-1,4-thiazin-5-one, m.p. 234°–236° C. The nmr and infrared spectra supported the proposed structure.

| Analysis | C | H | N |
|---|---|---|---|
| Calc'd. | 41.4 | 5.8 | 16.1 |
| Found | 41.2 | 5.9 | 15.9 |

EXAMPLE III

Preparation of 2-Oximino-3,3-dimethyltetrahydro-1,4-thiazin-5-one

A solution of 41 g α-aminoisobutyraldoxime hydrochloride and 150 ml. of water was charged into a stirred flask and cooled to 0° C. Chlorine was added to the solution at 0° C until 22 g. had been taken up. The reaction mixture was stirred at 0° C for 30 minutes after the chlorine addition. Sodium hydroxide (6 g in 40 ml water) was added with stirring to neutralize the hydrochloric acid, after which a solution of 36 g of ethyl mercaptoacetate and 12 g of sodium hydroxide in 40 ml of water was added rapidly at 5° to 10° C. The mixture was warmed to 25° C and stirred overnight. The solid product was filtered, washed with water then dried at room temperature, to yield 7 g of 2-oximino-3,3-dimethyltetrahydro-1,4-thiazin-5-one, m.p. 234°–236° C. An nmr spectrum and m.p. comparison showed the product to be identical with that from Example II.

EXAMPLE IV

Preparation of 2-Oximino-3,3-dimethyltetrahydro-1,4-thiazin-5-one

A mixture of 5.0 g 1-(ethoxycarbonylmethylthio)-2-methyl-2-(methylsulfonyl)propionaldoxime and 150 ml. of ammonium hydroxide was charged into a pyrex pressure bottle and stirred at room temperature for forty hours. The mixture was stripped of excess ammonia and water under reduced pressure. The solid crystalline residue was washed with water, then dried at room temperature to yield 3 g of 2-oximino-3,3-dimethyltetrahydro-1,4-thiazin-5-one, m.p. 234° C. The nmr spectrum was identical with those of the compounds from Examples II and III.

EXAMPLE V

Preparation of 2-[O-(Methylcarbamoyl)oximino]-3,3-dimethyltetrahydro-1,4-thiazin-5-one A solution of 3 g of 2-oximino-3,3-dimethyltetrahydro-1,4-thiazin-5-one, 2 g of methyl isocyanate, 100 ml of acetonitrile and 2 drops of triethylamine was charged into a pyrex pressure bottle and stirred at 28° C for 24 hours. The excess methyl isocyanate and acetonitrile was stripped from the product under reduced pressure. The white crystalline residue was recrystallized from isopropanol to yield 3g of 3,3-dimethyl-2-[O-(methylcarbamoyl)oximino]-3,3-dimethyltetrahydro-1,4-thiazin-5-one, m.p. 185°–188° C.

| Analysis | C | H | N |
|---|---|---|---|
| Calc'd. | 54.2 | 8.6 | 21.1 |
| Found | 54.0 | 8.6 | 20.9 |

EXAMPLE VI

Preparation of 2-Oximino-3,3,6-trimethyltetrahydro-1,4-thiazin-5-one

Utilizng the procedure of Example II 1-(ethoxycarbonylethylthio)-2-nitro-2-methylpropionaldoxime was treated with ammonium hydroxide to yield 4 g of 2-oximino-3,3,6-trimethyltetrahydro-1,4-thiazin-5-one, m.p. 199°–202° C. NMR supported the proposed structure.

| Analysis | C | H | N |
|---|---|---|---|
| Calc'd. | 44.7 | 6.4 | 14.9 |
| Found | 44.4 | 6.4 | 14.9 |

EXAMPLE VII

Preparation of 2-[O-(Methylcarbamoyl)oximino]-3,3,6-trimethyltetrahydro-1,4-thiazin-5-one Utilizing the procedure of Example V, 2-oximino-3,3,6-trimethyltetrahydro-1,4-thiazin-5-one was reacted with methyl isocyanate in the presence of trimethylamine to yield 3 g of 2-[O-(methylcarbamoyl)oximino]-3,3,6-trimethyltetrahydro-1,4-thiazin-5-one, m.p. 190°–191° C. IR spectrum supported the proposed structure.

| Analysis | C | H | N |
|---|---|---|---|
| Calc'd. | 44.1 | 6.2 | 17.1 |
| Found | 45.6 | 6.9 | 15.5 |

EXAMPLE VIII

Preparation of 2-Oximino-3,4-dimethyltetrahydro-1,4-thiazin-5-one

A solution of 5.6 g of sodium hydroxide, 100 ml of methanol and 100 ml of toluene was charged into a flask and stirred vigorously while adding 23 g of 2-(acetylthio)-N-methyl-N-(1-nitro-2-propyl)acetamide, over a 5 minute period at 30°-40° C. The reaction mixture was stirred at 40° C for 8 hours, then stirred overnight at room temperature. The mixture was stripped of solvents under reduced pressure. The solid residue was dissolved in 200 ml of water. The mixture was filtered and the filtrate was acidified with hydrochloric acid. The solid which precipitated was filtered, washed with water and dried at room temperature. The solid product was recrystallized from isopropanol to yield 5.0 g of 2-oximino-3,4-dimethyltetrahydro-1,4-thiazin-5-one, m.p. 205° C.

EXAMPLE IX

Preparation 2-[O-(methylcarbamoyl)oximino]-3,4-dimethyltetrahydro-1,4-thiazin-5-one Utilizing the procedure of Example V, 2-oximino-3,4-dimethyltetrahydro-1,4-thiazin-5-one was reacted with methyl isocyanate in the presence of triethylamine to yield 3 g of 2-[O-(methylcarbamoyl)oximino]-3,4-dimethyltetrahydro-1,4-thiazin-5-one, m.p. 161°-163° C.

| Analysis | C | H | N |
|---|---|---|---|
| Calc'd. | 41.5 | 5.7 | 18.2 |
| Found | 41.5 | 5.6 | 18.1 |

EXAMPLE X

Preparation of 2-Oximino-3-methyl-4-butyltetrahydro-1,4-thiazin-5-one

A solution of 6.8 g of sodium hydroxide, 125 ml of methanol, and 125 ml of toluene was charged to a flask and stirred vigorously while adding 33 g. of 2-(acetylthio)-N-butyl-N(1-nitro-2-propyl) acetamide over a 5-minute period of 30°-40° C. The reaction mixture was stirred at 40° C for 5 hours; then stirred overnight at room temperature. The mixture was stripped of solvents under reduced pressure. The solid residue was dissolved in 500 ml of cold water and the mixture was filtered and the filtrate was acidified with conc. hydrochloric acid. The resulting mixture was extracted three times with methylene chloride and the methylene chloride layer was dried with MgSO$_4$. The methylene chloride was stripped from product under reduced pressure. The oily residue crystallized over night. This crude reaction product was recrystallized from 60/40 xylene-hexane mixture to yield 12 g of 2-oximino-3-methyl-4-butyltetrahydro-1,4-thiazin-5-one, m.p. 118°-120° C. An nmr spectrum supported the proposed structure.

EXAMPLE XI

Preparation of 2-[O-(Methylcarbamoyl)oximino]-3-Methyl-4-butyltetrahydro-1,4-thiazin-5-one Utilizing the procedure of Example V, 2-oximino-3-methyl-4-butyltetrahydro-1,4-thiazin-5-one was reacted with methyl isocyanate in the presence of triethylamine to yield 7.0 of 2-[O-(methylcarbamoyl)oximino]-3-methyl-4-butyltetrahydro-1,4-thiazin-5-one, m.p. 118°-120° C. An nmr spectrum supported the proposed structure.

| Analysis | C | H | N |
|---|---|---|---|
| Calc'd. | 48.3 | 7.0 | 15.4 |
| Found | 48.6 | 7.0 | 15.2 |

EXAMPLE XII

Preparation of 2-[O-(N-methyl-N-trichloromethanesulfenylcarbamoyl)oximino]-3,3-dimethyltetrahydro-1,4-thiazin-5-one A mixture of 3.5 g of 2-oximino-3,3-dimethyltetrahydro-1,4-thiazin-5-one, dioxane and N-methyl-N-(trichloromethylthio)carbamoyl fluoride (4.5 g) was charged to a stirred flask and 2.1 g of triethylamine was added dropwise at 30° C, over a 2-minute period. The reaction mixture was stirred overnight at room temperature. The reaction mixture was then added to cold water and stirred for 10 minutes. The crystalline solid was filtered, washed thoroughly with water and dried overnight. After drying the crude product was recrystallized from isopropanol to yield 3 g of 2-[O-(N-methyl-N-trichloromethanesulfenylcarbamoyl)oximino]-3,3-dimethyltetrahydro-1,4-thiazin-5-one, m.p. 189°-190° C. The nmr spectrum of this material was consistent with its proposed structure.

| Analysis | C | H | N |
|---|---|---|---|
| Calc'd. | 28.4 | 3.2 | 11.0 |
| Found | 28.8 | 3.3 | 10.9 |

EXAMPLE XIII

Preparation of 2-[O-(N-Acetyl-N-methylcarbamoyl)oximino]-3,3-dimethyltetrahydro-1,4-thiazin-5-one Utilizing the procedure of Example XII, N-acetyl-N-methylcarbamic acid chloride was reacted with 2-oximino-3,3-dimethyltetrahydro-1,4-thiazin-5-one to yield 2-[O-(N-acetyl-N-methylcarbamoyl)oximino]-3,3-dimethyltetrahydro-1,4-thiazin-5-one, m.p. 218°-220° C. The nmr spectrum supported the proposed structure.

| Analysis | C | H | N |
|---|---|---|---|
| Calc'd. | 43.9 | 5.5 | 15.4 |
| Found | 44.0 | 5.2 | 15.4 |

EXAMPLE XIV

Preparation of
2-[O-(N-Methyl-N-morpholinosulfenylcarbamoyl)oximino]-3,3-dimethyltetrahydro-1,4-thiazin-5-one A mixture of 3.0 g of 2-oximino-3,3-dimethyltetrahydro-1,4-thiazin-5-one, benzene and N-methyl-N-(4-morpholinosulfenyl) carbamoyl fluorine 3.3 g was charged to a stirred flask and triethylamine was added dropwise at 30° C, with stirring and cooling, over a 2 minute period. The reaction mixture was heated and stirred at 70° C for 24 hours when it was cooled to 25° C and filtered. The filtrate was washed thoroughly with water and the benzene layer was dried with magnesium sulfate. The benzene was removed from the reaction mixture under reduced pressure. The crystalline residue was recrystallized from acetonitrile to provide 2 grams of 2-[O-(N-Methyl-N-morpholinosulfenylcarbamoyl)oximino]-3,3-dimethyltetrahydro-1,4-thiazin-5-one, m.p. 180°–182° C. An nmr spectrum supported the proposed structure.

| Analysis: | C | H | N |
|---|---|---|---|
| Calc'd. | 41.4 | 5.8 | 16.1 |
| Found | 41.2 | 6.1 | 15.8 |

EXAMPLE XV

Preparation of
2-[O-(N-Dimethylaminosulfenyl-N-methylcarbamoyl)oximino]-3,3-dimethyltetrahydro-1,4-thiazin-5-one A mixture of 5.8 g of 2-oximino-3,3-dimethyltetrahydro-1,4-thiazin-5-one, 200 ml dioxane, 2.1 g powdered potassium hydroxide and 0.1 g dicyclohexyl-18-crown-6, was charged to a stirred flask and 5.3 g of N-methyl-N-(dimethylaminosulfenyl)carbamoyl fluoride was added at 30° C over a 1-minute period. The reaction mixture was stirred overnight at room temperature and then added to cold water and stirred for 5 minutes. The resulting mixture was extracted with methylene chloride. The methylene chloride layer was washed thoroughly with water and then dried with magnesium sulfate. The methylene chloride was stripped from the product under reduced pressure and the crystalline residue was recrystallized from ethylene acetate to provide 7.0 g of 2-[O-(N-Dimethylaminosulfenyl-N-methylcarbamoyl)oximino]-3,3-dimethyltetrahydro-1,4-thiazin-5-one, m.p. 165°–167° C. An nmr spectrum supported the proposed structure.

| Analysis | C | H | N |
|---|---|---|---|
| Calc'd. | 39.2 | 5.9 | 18.3 |
| Found | 39.5 | 5.8 | 18.4 |

EXAMPLE XVI

Preparation of
N-Methyl-N-[4-(tert-butyl)phenylsulfenyl]carbamoyl fluoride

To 1200 ml of toluene at (—40°)–(20° C) in a one-gallon polypropylene bottle containing a stirrer, was added with stirring 37.4 grams (1.87 moles) of liquid hydrogen fluoride. The reaction mixture was raised to —10° C and 107 grams (1.87 moles) of methyl isocyanate was added with stirring and cooling. The reaction mixture was stirred for 1 hour at 0° C after the methyl isocyanate addition. To this mixture was then added 375 grams (1.87 moles) of 4-(tert-butyl) phenylsulfenyl chloride at 0° C over a 2 minute period. After the 4-(tert-butyl) phenylsulfenyl chloride addition, 189 grams (1.87 moles) of triethylamine was added slowly, with cooling and stirring. The reaction mixture was then warmed to 25° C and stirred overnight when it was added to 1000 ml of water. The toluene layer was washed four times with water and dried with magnesium sulfate after which it was distilled through a 1-foot packed column to give 275 grams of N-methyl-N-[4-(tert-butyl)phenylthio]carbamoyl fluoride, b.p. 122°/1.0 mm (yield 61%). The nmr spectrum agreed with the proposed structure.

EXAMPLE XVII

Preparation of N-Methyl-N-(4-Morpholinosulfenyl) carbamoyl Fluoride

Anhydrous hydrogen fluoride (3.4 g, 0.17 mole) was added to 200 ml of toluene at —10° C. in a polyethylene reactor equipped with a stainless steel stirrer and thermocouple well, and a polyethylene dry ice condenser. Methyl isocyanate (9.35 g, 0.17 mole) was then added dropwise; the temperature was maintained at —10° C. or less. Then, 26.3 g (0.17 mole) of freshly distilled 4-morpholinosulfenyl chloride was added to the mixture over a 20 minute period, and finally, 17.3 g (0.17 mole) triethylamine was added at —10° C. After the addition was completed the mixture was stirred and allowed to warm to room temperature for 30 minutes. It was filtered and the toluene filtrate was extracted twice with water and dried with magnesium sulfate. The toluene was removed in vacuo, and the residue was dissolved in boiling hexane, treated with decolorizing charcoal, filtered, and chilled. The resulting crystals were collected by suction filtration, and dried in vacuo to give 20 g. of N-methyl-N-(4-morpholinosulfenyl) carbamoyl fluoride m.p. 48°–50° C. (60.5 percent yield).

EXAMPLE XVIII

Preparation of
N-Methyl-N-(1-Piperidinosulfenyl)Carbamoyl Fluoride

Anhydrous hydrogen fluoride (10.0 g, 0.5 mole) was added to 400 ml of methylene chloride at —10° C in a polyethylene reactor fitted with a stainless steel stirrer and a thermocouple well. To this solution was added 28.6 g (0.5 mole) of methyl isocyanate in 15 min. at —10° C. The mixture was stirred for 20 min. To the mixture was then added 1-piperidinosulfenyl chloride, prepared in situ by evaporating 18.0 g (0.25 mole) of chlorine into a slurry of 58.1 g (10.25 mole) of 1,1'-dithiobispiperidine in 150 ml of methylene chloride at —10° C, followed by stirring the mixture for 0.5 hr, and then sparging it with nitrogen for 20 min. to remove the excess chlorine. Triethylamine (50.6 g, 0.5 mole) was added dropwise to the above mixture at —10° C. The mixture was stirred for 0.5 hr. and then allowed to warm to 0° C. After the addition of 250 ml of water, the methylene chloride layer was agitated thoroughly and was washed once again with 250 ml of water, dried over anhydrous magnesium sulfate, filtered and concentrated to give 61 g reddish liquid residue. Distillation of the residue at 74°–76° C/0.38 mm yielded 44.2 g of N-methyl-N-(1-piperidinosulfenyl carbamoyl fluoride (46%) as an amber liquid.

Infrared: $3.5\mu$ (N—$CH_2$); $5.6\mu$ (C=O); $7.05\mu$ (N—$CH_3$); $7.78\mu$ (C—F)

NMR (CDCl$_3$): α1.52 (m, 6H, —CH$_2$—β and γ to N); α3.28 (m, 4H, —CH$_2$—γ to N); α3.35 (α, J = 1Hz, 3H, N—CH$_3$)

Anal. Calculated for CH$_{13}$FN$_2$OS: C, 43.73; H, 6.81; N, 14.57. Found: C, 43.57; H, 6.50; N, 14.44.

EXAMPLE XIX

Preparation of N-Methyl-N-(Diethylaminosulfenyl) carbamoyl Fluoride

Anhydrous hydrogen fluoride (3.0 g, 0.15 mole) was added to 150 ml of methylene chloride at −10° C. Then 8.6 g of methylisocyanate was added, followed by 20.9 g (0.15 mole) of N,N-diethylaminosulfenyl chloride at 0° C. Triethylamine (15.2 g) was then added at 0° C over a 15-minute period, and the mixture was stirred at +5° C for 1 hour. The mixture was then extracted with water (100 ml), saturated sodium bicarbonate solution, and water again. After drying (MgSO$_4$), the solvent was removed in vacuo, and the crude residue was vacuum distilled to give 17 g of N-methyl-N-(diethylaminosulfenyl carbamoyl fluoride, b.p. 57° C/0.8 mm (62.9 percent yield).

Anal. Calc'd. for C$_6$H$_{13}$FN$_2$O$_5$: C, 39.98; H, 7.27; N, 15.54. Found: C, 39.82; H, 6.83; N, 14.95.

EXAMPLE XX

Preparation of N-Phenyl-N-(4-Morpholinosulfenyl) carbamoyl Fluoride

Anhydrous hydrogen fluoride (4.0g) was added to methylene chloride (150 ml) at −10° C in a polyethylene reactor. Phenyl isocyanate (23.8 g, 0.2 mole) was then added dropwise over a 20 minute period. This mixture was stirred at 5° C for 1 hour, and then a solution of 30.6 g (0.2 mole) of 4-morpholinosulfenyl chloride in 75 ml of methylene chloride was added rapidly. Triethylamine (20.2 g) was then added slowly at −10° C. The mixture was then stirred and warmed to 0° C. for 1 hr., water extracted twice, dried (MgSO$_4$), and concentrated in vacuo. The resulting dark residue was vacuum distilled to remove volatile impurities, and then the kettle residue was extracted with hot hexane. The hexane solution upon cooling deposited 6 g of N-phenyl-N-(4-morpholinosulfenyl) carbamoyl fluoride, m.p. 71°–72° C, (11 percent yield).

Infrared: 5.6μ, C=O.

NMR: CDCl$_3$; multiplets at α3.25 and 3.66 ppm (4H each); single at α7.36 ppm (5H).

Anal. Calc'd. for C$_{11}$H$_{13}$FN$_2$O$_2$S: C, 51.55; H, 5.11; N, 10.93. Found: C, 52.27; H, 5.41; N, 10.94.

The following compounds are representative of other compounds that are within the scope of this invention which can be prepared according to this invention by selecting appropriate starting materials:

2-[O-(N-Trichloromethylsulfenyl-N-methylcarbamoyl)oximino]-4-methyltetrahydro-1,4-thiazin-5-one.

2-[O-(N-Trichloromethylsulfenyl-N-methylcarbamoyl)oximino]-4-methyltetrahydro-1,4-thiazin-5-one.

2-[O-(N-Trifluoromethanesulfenyl-N-methylcarbamoyl)oximino]-4-isopropyltetrahydro-1,4-thiazin-5-one.

2-[O-(N-(4-t-Butylphenylsulfenyl)-N-methylcarbamoyl]-3,4-dimethyltetrahydro-1,4-thiazin-5-one.

2-[O-[N-(2,4-Dimethylphenylsulfenyl)-N-methylcarbamoyl]oximino]-4-methyltetrahydro-1,4-thiazin-5-one.

2-[O-[N-(4-Chlorophenylsulfenyl)-N-methylcarbamoyl]oximino]-3,4,6-trimethyltetrahydro-1,4-thiazin-5-one.

2-[O-(N-Phenylsulfenyl-N-methylcarbamoyl)oximino]-4-methyltetrahydro-1,4-thiazin-5-one.

2-[O-(N,N-Diisopropylcarbamoyl)oximino]-4-methyltetrahydro-1,4-thiazin-5-one.

2-[O-(2-Chloroethylcarbamoyl)oximino]-3,3-dimethyltetrahydro-1,4-thiazin-5-one.

2-[O-(2-Methoxymethylcarbamoyl)oximino]-3,3-dimethyltetrahydro-1,4-thiazin-5-one.

2-[O-(1-Cyanoethylcarbamoyl)oximino]-3,3-dimethyltetrahydro-1,4-thiazin-5-one.

2-[O-(2-Nitropropylcarbamoyl)oximino]-3,3-dimethyltetrahydro-1,4-thiazin-5-one.

2-[O-(2-Methylthioethylcarbamoyl)oximino]-3,3-dimethyltetrahydro-1,4-thiazin-5-one.

2-[O-(2-Ethylsulfinylethylcarbamoyl)oximino]-3,3-dimethyltetrahydro-1,4-thiazin-5-one.

2-[O-(2-Methylsulfonylpropylcarbamoyl)oximino]-3,3-dimethyltetrahydro-1,4-thiazin-5-one.

2-Oximinotetrahydro-1,4-thiazin-5-one.

2-[O-(Methylcarbamoyl)oximino]tetrahydro-1,4-thiazin-5-one.

2-[O-(Dimethylcarbamoyl)oximino]tetrahydro-1,4-thiazin-5-one.

2-[O-(Carbamoyl)oximino]-3-ethyltetrahydro-1,4-thiazin-5-one.

2-[O-(Allylcarbamoyl)oximino]-3,6-dimethyltetrahydro-1,4-thiazin-5-one.

2-[O-(Phenylcarbamoyl)oximino]-4-methyltetrahydro-1,4-thiazin-5-one.

2-[O-(4-Chlorophenylcarbamoyl)oximino]-4,6-dimethyltetrahydro-1,4-thiazin-5-one.

2-[O-(N-Isopropyl-N-methylcarbamoyl)oximino]-3,3-dimethyltetrahydro-1,4-thiazin-5-one.

2-[O-(N-Methyl-N-propargylcarbamoyl)oximino]-3-methyltetrahydro-1,4-thiazin-5-one.

2-[O-(Benzylcarbamoyl)oximino]-3-butyltetrahydro-1,4-thiazin-5-one.

2-[O-(N-Acetyl-N-methylcarbamoyl)oximino]-3-methyl-4-ethyltetrahydro-1,4-thiazin-5-one.

2-[D-(N-Butyryl-N-methylcarbamoyl)oximino]-3-methyltetrahydro-1,4-thiazin-5-one.

2-[O-[N-(2'-Methylsulfonylphenyl)-N-methylcarbamoyl]oximino]tetrahydro-1,4-thiazin-5-one.

2-[O-[N-(2'-Dimethylamino-4'-methoxyphenylsulfenyl)-N-methylcarbamoyl]oximino]tetrahydro-1,4-thiazin-5-one.

2-[O-[N-(2'-Methylthiophenylsulfenyl)-N-ethylcarbamoyl]oximino]-4-methyltetrahydro-1,4-thiazin-5-one.

2-[O-[N-(2'-Nitro-4'-cyano-6'-trifluoromethylphenylsulfenyl)-N-methylcarbamoyl]oximino]-6-isopropyltetrahydro-1,4-thiazin-5-one.

2-[O-[N-(4'-Methylsulfonylphenylsulfenyl)-N-methylcarbamoyl]oximino]tetrahydro-1,4-thiazin-5one.

2-[O-(N-Hex-3-ene-N-propylcarbamoyl)oximino]-4-propyltetrahydro-1,4-thiazin-b 5-one.

2-[O-(N-Hept-3-yne-N-methylcarbamoyl)oximino]-3,3,4,6,6-pentamethyltetrahydro-1,4-thiazin-5-one.

2-[O-[N-(3'-Phenylpropyl)-N-ethylcarbamoyl]oximino]-3,6-dipropyltetrahydro-1,4-thiazin-5-one.

2-[O-[N-(2'-Fluoro-3'-Bromopropyl)-N-methylcarbamoyl]oximino]-3,3-dimethyltetrahydro-1,4-thiazin-5-one.

2-[O-[N-Dimethylaminocarbonyl)-N-methylcarbamoyl]oximino]-6-methyltetrahydro-1,4-thiazin-5-one.
2-[O-(N-Aminocarbonylcarbamoyl)-oximino]tetrahydro-1,4-thiazin-5-one.
2-Oximino-4-hexyltetrahydro-1,4-thiazin-5-one.
2-Oximino-3,3,4,6,6-pentamethyltetrahydro-1,4-thiazine-5-one.
2-Oximino-3-methyl-4-t-butyl-6-ethyltetrahydro-1,4thiazin-5-one.
2-Oximino-3,3-dimethyltetrahydro-1,4-thiazin-5-one.
2-Oximino-4-methyltetrahydro-1,4-thiazin-5-one.
2-Oximino-4-isopropyltetrahydro-1,4-thiazin-5-one.
2-Oximino-4,6-dimethyltetrahydro-1,4-thiazin-5-one.
2-Oximino-3,6-dipropyltetrahydro-1,4-thiazin-5-one.
2-Oximino-3,4-dihexyl-6-octyltetrhydro-1,4-thiazin-5-one.
2-[O-[N-(1-Pyrrolidylsulfenyl)carbamoyl)-N-methylcarbamoyl]oximino]-4,6-dimethyltetrahydro-1,4-thiazin-5-one.
2-[O-[N-(1-Piperidylsulfenyl)-N-methylcarbamoyl]oximino]-4-isopropyltetrahydro-1,4-thiazin-5-one.
2-[O-[N-(2'-Nitro-4'-cyanophenyl)-N-ethylcarbarbamoyl]oximino]tetrahydro-1,4-thiazin-5-one.
2-[O-[N-(4'-Methoxyphenyl)-N-allylcarbamoyl]oximino]tetrahydro-1,4-thiazin-5-one.
2-[O-[N-(2'-Methylaminocarbonyl-4'-methylthiophenyl)-N-isopropylcarbamoyl]oximino]-4-methyltetrahydro-1,4-thiazin-5-one.
2-[O-[N-(4'-Methylsulfonylphenylsulfenyl)-N-(4'-methylsulfinylphenyl)carbamoyl]oximino]tetrahydro-1,4thiazin-5-one.
2-[O-(4'-Methylaminocarbonylphenylcarbamoyl)oximino]-6-methyltetrahydro-1,4-thiazin-5-one.
2-[O-(2'-Aminocarbonylphenylcarbamoyl)oximino]tetrahydro-1,4-thiazin-5-one.

Selected species of the new compounds were evaluated to determine their pesticidal activity against mites and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of test compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulated by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (Prodenia eridania, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae cound easily consume the whole leaf within 24 hours, no more food was added. Larvae which were unable to move the length of the body, even upon stimulation by prodding, were considered dead. Percent mortality was recovered for various concentration levels.

Mexican Bean Beetle Leaf Spray Test

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formation. Potted Tendergreen bean plants of standard height and age were placed on a revolving turntable and sprayed with 100–110 milliliters of test compound formulated by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (Musca domestica, L.), reared according to the specifications of the Chemical Specialities Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and 25 immobilized individuals, males and females, were transferred to a cage consisting of a standard food strainer about 5 inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a souffle cup containing a 1-inch square of an absorbent cotton pad. This bait cup was introduced and centered on the blotting paper under the food strainer prior to admitting the anesthetized flies. The caged flies were allowed to feed on the bait for 24 hours, at a temperature of 80°±5° F. and the relative humidity of 50±5 percent. Flies which showed no sign of movement on prodding were considered dead.

Mite Foliage Spray Test

Adults and nymphal stages of the two-spotted mite (Tetranychus urticae Koch), reared on Tengergreen bean plants at 80±5 percent relative humidity, were the test organisms. Infested leaves from a stock culture were placed on the primary leaves of two bean plants 6 to 8 inches in height, growing in a 2½ inch clay pot. 150-200 Mites, a sufficient number for testing, transferred from the excised leaves to the fresh plants in a period of 24 hours. Following the 24 hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considering living.

The results of these tests are set forth in Table I below. In these tests the pesticidal activity of the compounds against aphid, mite, Southern Armyworm, Mexican Bean Beetle, and house fly was rated as follows:

A = Excellent control
B = Partial control
C = No control

Certain of these compositions were also evaluated to determine their peroral toxicity to mammals. The animal selected for this experiment was the rat. The test results obtained are expressed in terms of the number of milligrams of compositions per kilogram of weight of the animal required to achieve a mortality rate of 50 percent ($LD_{50}$).

The results of all of these tests together with physical properties of the tested compounds are set forth in Table 1 below:

TABLE I

Physical, Biological and Analytical Properties of the Compounds of this Invention

| Compound | MP ° C | Spectral Data | | Biological Activity | | | | | Rat $LD_{50}$ (mg/kg) |
|---|---|---|---|---|---|---|---|---|---|
| | | NMR | IR | Aphid | Mite | Southern Armyworm | Mexican Bean Beetle | House Fly | |
| 2-[O-(Methylcarbamoyl)oximino]-3,3-dimethyltetrahydro-1,4-thiazin-5-one | 185-188 | a | a | A | A | A | A | A | 1.11 |
| 2-Oximino-3,3-dimethyltetrahydro-1,4-thiazin-5-one | 234-236 | a | a | — | — | — | — | — | — |
| 2-Oximino-3,3,6-trimethyltetrahydro-1,4-thiazin-5-one | 199-202 | a | a | — | — | — | — | — | — |
| 2-[O-(Methylcarbamoyl)oximino-]3,3,6-trimethyltetrahydro-1,4-thiazin-5-one | 190-191 | a | a | A | A | B | A | A | 0.884 |
| 2-Oximino-3-methyltetrahydro-1,4-thiazin-5-one | 182-185 | a | — | — | — | — | — | — | — |
| 2-[O-(Methylcarbamoyl)oximino]-3-methyltetrahydro-1,4-thiazin-5-one | 155-158 | a | a | B | A | A | A | A | 5.66 |
| 2-Oximino-3,4-dimethyltetrahydro-1,4-thiazin-5-one | 205 | a | — | — | C | C | C | C | — |
| 2-[O-(Methylcarbamoyl)oximino]-4-butyl-3-methyltetrahydro-1,4-thiazin-5-one | 118-120 | a | a | C | C | C | B | B | — |
| 2-Oximino-4-isopropyl-3-methyltetrahydro-1,4-thiazin-5-one | 187-190 | a | — | — | — | — | — | — | — |
| 2-[O-(Methylcarbamoyl)oximino]-4-isopropyl-3-methyltetrahydro-1,4-thiazin-5-one | 172-174 | a | — | C | B | C | C | A | — |
| 2-Oximino-4-isobutyl-3-methyltetrahydro-1,4-thiazin-5-one | 155-158 | a | — | C | C | C | C | C | — |
| 2-[O-(Methylcarbamoyl)oximino]-4-isobutyl-3-methyltetrahydro- | 90-92 | a | — | C | C | C | C | A | — |

TABLE I-continued
Physical, Biological and Analytical Properties of the Compounds of this Invention

| Compound | MP ° C | Spectral Data NMR | IR | Aphid | Mite | Southern Armyworm | Mexican Bean Beetle | House Fly | Rat $LD_{50}$ (mg/kg) |
|---|---|---|---|---|---|---|---|---|---|
| 1,4-thiazin-5-one 2-[O-(N-Trichloromethanesulfenyl-N-methylcarbamoyl)oximino]-3,4-dimethyltetrahydro-1,4-thiazin-5-one | 189–190 | a | — | B | A | B | A | A | 3.54 |
| 2-[O-(Methylcarbamoyl)oximino]-3,4-dimethyltetrahydro-1,4-thiazin-5-one | 161–163 | a | — | A | A | C | A | A | — |
| 2-Oximino-3,3,4-trimethyltetrahydro-1,4-thiazin-5-one | 232–236 | a | — | C | C | C | C | C | — |
| 2-[O-(Methylcarbamoyl)oximino]-3,3,4-trimethyltetrahydro-1,4-thiazin-5-one | 155–158 | a | a | B | A | B | A | A | — |
| 2-Oximino-4-ethyl-3-methyltetrahydro-1,4-thiazin-5-one | 173–175 | a | — | C | C | C | C | C | — |
| 2-[O-(Methylcarbamoyl)oximino]-4-ethyl-3-methyltetrahydro-1,4-thiazin-5-one | 148–150 | a | a | B | A | B | B | A | — |
| 2-Oximino-4-butyl-3-methyltetrahydro-1,4-thiazin-5-one | 118–120 | a | a | C | C | C | C | C | — |
| 2-[O-(N-Acetyl-N-methylcarbamoyl)-oximino]-3,4-dimethyltetrahydro-1,4-thiazin-5-one | 218–220 | a | — | C | C | A | C | C | — |
| 2-[O-(N-Morpholinosulfenyl-N-methylcarbamoyl)oximino]-3,3-dimethyltetrahydro-1,4-thiazin-5-one | 180–182 | a | — | A | — | A | A | A | — |
| 2-[O-(N-Dimethylaminosulfenyl-N-methylcarbamoyl)oximino]-3,3-dimethyltetrahydro-1,4-thiazin-5-one | 165–167 | a | — | A | A | A | A | A | — | a) agrees with structure

The insects tested are merely representative of a broader group of insects which can be controlled by the carbamate compounds of this invention. For example, the compounds of this invention demonstrated noteworthy activity against nematodes.

The carbamate compounds contemplated in this invention may be applied as insecticides, miticides and nematocides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water and the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In for formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary fromabout 10 to 95 per cent by weight and in the solid formulations from about 0.5 to about 90 per cent by weight. Satisfactory sprays, dusts, or granules for general use contain from about ¼ to 15 pounds of active toxicant per acre.

The pesticides contemplated herein prevent attack by insects, nematodes and mites upon plants or other materials to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the present of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seed, or the roots of plants without injuring either the seeds or roots of plants. They may also be used in combination with other pesticidally active compounds.

What is claimed is:

1. A compound of the formula:

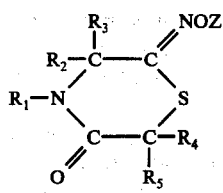

wherein:

$R_1$, $R_2$, $R_3$, $R_4$ and $R_5$ are individually hydrogen or alkyl

Z is hydrogen or

wherein:

$R_6$ and $R_7$ are individually hydrogen, alkenyl, alkynyl, phenylalkyl or either substituted or unsubstituted alkyl or phenyl wherein the permissible substituents are one or more fluoro, chloro, bromo, nitro, cyano, alkyl, alkoxy, alkylthio, alkylsulfinyl, alkysulfonyl, carbamonyl, alkylcarboamoyl, or dialkylcarbamoyl substitutes; or when $R_6$ is other than hydrogen $R_7$ may also be alkanoyl, trihalomethanesulfenyl, dialkylaminosulfenyl, morpholinosulfenyl, pyrrolidylsulfenyl, piperidylsulfenyl or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl or alkylsulfonyl substituents in any combinations; with the proviso that $R_1$, $R_2$, $R_3$, $R_4$ and $R_5$ substituents individually may not include more than eight aliphatic carbon atoms and $R_6$ and $R_7$ substituents individually may not include more than 18 carbon atoms.

2. A compound according to claim 1 wherein Z is hydrogen.

3. A compound according to claim 1 wherin Z is

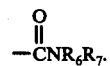

4. A compound according to claim 1 wherein $R_1$, $R_2$, $R_3$, $R_4$, and $R_5$ are individually hydrogen, methyl or ethyl.

5. A compound according to claim 1 wherein $R_1$, $R_2$, $R_3$, $R_4$ and $R_5$ substitutents are individually hdrogen or methyl, provided that not more than three substituents may be methyl.

6. A compound according to claim 1 wherien $R_1$, $R_2$, $R_3$, $R_4$, $R_5$, are hydrogen.

7. A compound according to claim 1 wherein $R_6$ is alkyl.

8. A compound according to claim 1 wherein $R_6$ is methyl.

9. A compound according to claim 1 wherein $R_7$ is hydrogen, alkyl, alkenyl, trihalomethanesulfenyl, dialkylaminosulfenyl, morpholinosulfenyl, pyrrolidylsulfenyl, piperidylsulfenyl, or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl or alkylsulfonyl substitutents.

10. A compound according to claim 1 wherein $R_6$ is methyl and $R_7$ is hydrogen, morpholinosulfenyl, trihalomethanesulfenyl or dialkylaminosulfenyl.

11. 2-[-O-(Methylcarbamoyl) oximino]-3,4-dimethyltetrahydro-1,4-thiazin-5-one.

12. 2-[0-(N-Dimethylaminosulfenyl-N-methylcarbamoyl) oximinol)-3,3]-dimethyltetrahydro-1,4-thiazin-5-one.

13. 2-[0-[N-(4'-Morpholinosulfenyl)-N-methylcarbamoyl]oximino]-3,3-dimethyltetrahydro-1,4-thiazin-5-one.

14. 2-[O-(Dimethylcarbamoyl) oximino]-3,3-dimethyltetrahydro-1,4-thiazin-5-one.

15. 2-[0-(Methylcarbamoyl) oximino]-3-methyl tetrahydro-1,4-thiazin-5-one.

16. 2-Oximino-3-methyltetrahydro-1,4-thiazin-5-one.

17. 2-Oximino-3,3-dimethyltetrahydro-1,4-thiazin-5-one.

18. 2-Oximino-3,4-dimethyltetrahydro-1,4-thiazin-5-one.

19. A miticidal and insecticidal composition comprising an acceptable carrier and as active toxicant a compound of the formula

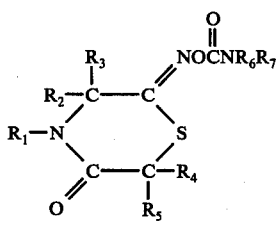

wherein $R_1$, $R_2$, $R_3$, $R_4$, and $R_5$ are individually hydrogen or alkyl;

$R_6$ and $R_7$ are individually hydrogen, alkenyl, alkynyl, phenylalkyl or either substituted or unsubstituted alkyl or phenyl wherein the permissible substituents are one or more fluoro, chloro, bromo, nitro, cyano, alkyl, alkoxy, alkylthio, alkylsulfinyl, alkylsulfonyl, carbamoyl, alkylcarbamoyl, or dialkylcarbamoyl substituents in any combination; or when $R_6$ is other than hydrogen $R_7$ may also be alkanoyl, trihalomethanesulfenyl, dialkylaminosulfenyl, morpholinosulfenyl, pyrrolidylsulfenyl, piperidylsulfenyl or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl or alkylsulfonyl substituents in any combination;

with the proviso the $R_1$, $R_2$, $R_3$, $R_4$ and $R_5$ substituents individually may not include more than eigth aliphatic carbons atoms and $R_6$ and $R_7$ substituents individually may not include more than 18 carbon atoms.

20. A composition according to claim 19 wherein $R_1$, $R_2$, $R_3$, $R_4$ and $R_5$ are individually hydrogen, methyl or ethyl.

21. A composition according to claim 19 wherein $R_1$, $R_2$, $R_3$, $R_4$ and $R_5$ are individually hydrogen or methyl provided that not more than three substituents may be methyl.

22. A composition according to claim 19 wherein $R_1$, $R_2$, $R_3$, $R_4$ and $R_5$ are hydrogen.

23. A composition according to claim 19 wherein $R_6$ is alkyl.

24. A composition according to claim 19 whrein $R_6$ is methyl.

25. A composition according to claim 19 wherein $R_7$ is hydrogen, alkyl, alkenyl, trihalomethanesulfenyl, dialkylaminosulfenyl, morpholinosulfenyl, pyrrolidylsulfenyl, piperidylsulfenyl or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl or alkylsulfonyl substituents.

26. A composition according to claim 19 wherein $R_6$ is methyl and $R_7$ is hydrogen morpholinosulfenyl, trihalomethanesulfenyl or dialklaminosulfenyl.

27. A composition according to claim 19 wherein the active toxicant is 2-[O-(dimethylcarbamoyl)oximino]-3,3-dimethyltetrahydro-1,4-thiazin-5-one.

28. A composition according to claim 19 wherein the active toxicant is 2-[O-(methylcarbamoyl)oximino]-3-methyltetrahyro-1,4-thiazin-5-one.

29. A composition according to claim 19 wherein the active toxicant is 2-[O-(methylcarbamoyl)oximino]-3,4-dimethyltetrahydro-1,4-thiazin-5-one.

30. A composition according to claim 19 wherein the active toxicant is 2-[O-(N-dimethylaminosulfenyl-N-methylcarbamoyl)oximino]-3,3-dimethyltetrahydro-1,4-thiazin-5-one.

31. A composition according to claim 19 wherein the active toxicant is 2-[O-[N-(4-morpholinosulfenyl)-N-methylcarbamoyl]oximino]-3,3-dimethyltetrahydro-1,4-thiazin-5-one.

32. A method of controlling insects and mites which comprises subjecting them to an insecticidally or miticidally effective amount of a compound of the formula:

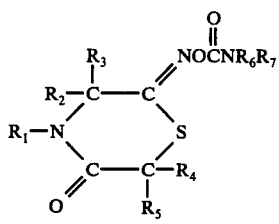

wherein:
$R_1$, $R_2$, $R_3$, $R_4$ and $R_5$ are individually hydrogen or alkyl;
$R_6$ and $R_7$ are individually hydrogen, alkenyl, alkynyl, phenylalkyl or either substituted or unsubstituted alkyl or phenyl wherein the permissible substituents are one or more fluoro, chloro, bromo, nitro, cyano, alkyl, alkoxy, alkylthio, alkylsulfinyl, alkylsulfonyl, carbamoyl, alkylcarbamoyl, or dialkylcarbamoyl substituents in any combination ; or when $R_6$ is other than hydrogen $R_7$ may also be alkanoyl, trihalomethanesulfenyl, dialkylaminosulfenyl, morpholinosulfenyl, pyrrolidylsulfenyl, piperidylsulfenyl, or either substituted or unsubstituted phenylsulfenyl wherein the permissible substituents are one or more fluoro, chloro, bromo, nitro, cyano, alkoxy, alkyl trihalomethyl, alkylthio, alkylsulfinyl or alkylsulfonyl substituents in any combination; with the proviso that $R_1$, $R_2$, $R_3 R_4$ and $R_5$ substituents individually may not include more than eight aliphatic carbon atoms and $R_6$ and $R_7$ substituents individually may not include more than eighteen carbon atoms.

33. A method according to claim 32 wherein $R_1$, $R_2$, $R_3$, $R_4$ and $R_5$ are individually hydrogen methyl or ethyl.

34. A method according to claim 32 wherein $R_1$, $R_2$, $R_3$, $R_4$ and $R_5$ are individually hydrogen or methyl provided that not more than three substituents may be methyl.

35. A method according to claim 32 wherein $R_1$, $R_2$, $R_3$, $R_4$ and $R_5$ are hydrogen.

36. A method according to claim 32 wherein $R_6$ is alkyl.

37. A method according to claim 32 wherein $R_6$ is methyl.

38. A method according to claim 32 wherein $R_7$ is hydrogen, alkyl, alkenyl, trihalomethanesulfenyl, dialkylaminosulfenyl, morpholinosulfenyl, pyrrolidylsulfenyl, piperidylsulfenyl or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl, or alkylsulfonyl substituents.

39. A method according to claim 32 wherein $R_6$ is methyl and $R_7$ is hydrogen, morpholinosulfenyl, trihalomethanesulfenyl or dialkylaminosulfenyl.

40. A method according to claim 32 wherein the compound is 2-[O-(dimethylcarbamoyloximino)]-3,3-dimethyltetrahydro-1,4-thiazin-5-one.

41. A method according to claim 32 wherein the compound is 2-[O-(methylcarbamoyl)oximino]-3-methyltetrahydro-1,4-thiazin-5-one.

42. A method according to claim 32 wherein the compound is 2-[O-(methylcarbamoyl)oximino]-3,4-dimethyltetrahydro-1,4-thiazin-5-one.

43. A method according to claim 32 wherein the compound is 2-[O-(N-dimethylaminosulfenyl-N-methylcarbamoyl)oximino]-3,3-dimethyltetrahydro-1,4-thiazin-5-one.

44. A method according to claim 32 wherein the compound is 2-[O-[N-(4-morpholinosulfenyl)-N-methyl-yl-carbamoyl]oximino]-3,3-dimethyltetrahydro-1,4-thiazin-5one.

45. A method of preparing a compound of the formula

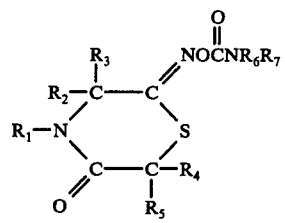

which comprises reacting a compound of the formula:

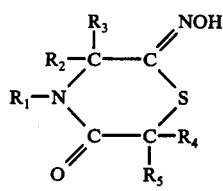

with a compound of the formula

in the presence of an acid acceptor wherein:
X is chlorine or fluorine;
$R_1$, $R_2$, $R_3$, $R_4$ and $R_5$ are individually hydrogen or alkyl;
$R_6$ and $R_7$ are individually hydrogen alkenyl, alkynyl, phenylalkyl or either substituted or unsubstituted alkyl or phenyl wherein the permissible substituents are one or more fluoro, chloro, bromo, nitro, cyano, alkyl, alkylthio, alkylsufinyl, alkylsulfonyl, carbamoyl, alkylcarbamoyl, or dialkylcarbamoyl substituents, or when $R_6$ is other than hydrogen $R_7$ may also be alkanoyl, trihalomethanesulfenyl, dialkylaminosulfenyl, morpholinosulfenyl, pyrrolidylsulfenyl, piperidylsulfenyl, or either substituted or unsubstituted phenylsulfenyl wherein the permissible substituents are one or more fluoro, chloro, bromo, nitro, cyano, alkoxy, alkyl, trihalomethyl, alkylthio, alkylsulfinyl or alkylsulfonyl substituents in any combination;

with the proviso that $R_1$, $R_2$, $R_3$, $R_4$ and $R_5$ substituents individually may not include more than eight aliphatic carbon atoms and $R_6$ and $R_7$ substituents individually may not include more than eighteen carbon atoms.

46. A method of preparing a compound of the formula:

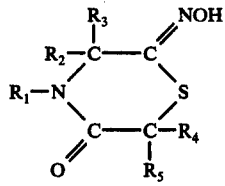

which compound of the formula:

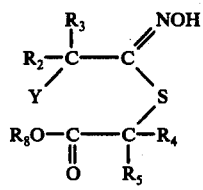

with an appropriately substituted amine compound of the formula:

$H_2NR_1$
wherein:
Y is nitro, methylsulfonyl or any other appropriate leaving group;
$R_1$, $R_2$, $R_3$, $R_4$ and $R_5$ are individually hydrogen or alkyl;
$R_8$ is alkyl;
with the proviso that $R_1$, $R_2$, $R_3$, $R_4$, $R_5$ and $R_8$ substituents individually may not include more than light aliphatic carbon atoms.

* * * * *

UNITED STATES PATENT OFFICE
CERTIFICATE OF CORRECTION

Patent No. 4,071,627      Dated January 31, 1978

Inventor(s) John A. Durden, Jr.

It is certified that error appears in the above-identified patent and that said Letters Patent are hereby corrected as shown below:

Column 1, lines 30 to 37 which read, -- alkali; wherein $$-\overset{\overset{O}{\|}}{C}NR_6R_7,$$

Z is hydrogen or -- should read,

"alkyl;

$$Z \text{ is hydrogen or } -\overset{\overset{O}{\|}}{C}NR_6R_7, \text{ wherein:"}$$

Column 7, line 24 which reads, -- $MgSO_3$ -- should read, "$MgSO_4$".

Column 9, line 29, which reads -- Preparation -- should read, "Preparation of".

UNITED STATES PATENT OFFICE
CERTIFICATE OF CORRECTION

Patent No. 4,071,627    Dated January 31, 1978

Inventor(s) John A. Durden, Jr.

It is certified that error appears in the above-identified patent and that said Letters Patent are hereby corrected as shown below:

Column 14, line 44, which reads -- 2[D-(N-...-- should read, "2-[O-(N-...".

Column 16, line 45, which reads --...cound...-- should read, "...could...".

Column 16, line 60, which reads --...formation...-- should read, "...formulation...".

Column 21, line 25 which reads, --...carbamonyl...-- should read, "...carbamoyl...".

UNITED STATES PATENT OFFICE
CERTIFICATE OF CORRECTION

Patent No. 4,071,627  Dated January 31, 1978

Inventor(s) John A. Durden, Jr.

It is certified that error appears in the above-identified patent and that said Letters Patent are hereby corrected as shown below:

Column 21, line 26, which reads --...carboamoyl...-- should read, "...carbamoyl...".

Column 22, line 57, which reads, --...eigth...-- should read, "...eight...".

Signed and Sealed this

Third Day of October 1978

[SEAL]

Attest:

RUTH C. MASON  
Attesting Officer

DONALD W. BANNER  
Commissioner of Patents and Trademarks